United States Patent
Watanabe et al.

(10) Patent No.: US 7,029,177 B2
(45) Date of Patent: Apr. 18, 2006

(54) X-RAY DIAGNOSIS APPARATUS

(75) Inventors: Izumi Watanabe, Tochigi-ken (JP);
Makoto Kaneko, Tochigi-ken (JP);
Hisayuki Uehara, Tochigi-ken (JP);
Akio Tetsuka, Tochigi-ken (JP);
Kazutoyo Hirayama, Tochigi-ken (JP);
Akiko Yamahana, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 213 days.

(21) Appl. No.: 10/662,511

(22) Filed: Sep. 16, 2003

(65) Prior Publication Data

US 2004/0131154 A1 Jul. 8, 2004

(30) Foreign Application Priority Data

Sep. 20, 2002 (JP) ............................. 2002-274288

(51) Int. Cl.
*H05G 1/02* (2006.01)
(52) U.S. Cl. ........................................ 378/197; 378/62
(58) Field of Classification Search ........ 378/195–198, 378/62
See application file for complete search history.

(56) References Cited

U.S. PATENT DOCUMENTS 5,040,199 A * 8/1991 Stein ........................... 378/56
5,369,678 A * 11/1994 Chiu et al. ..................... 378/62
6,055,295 A * 4/2000 Murthy et al. ............... 378/151
6,845,142 B1 * 1/2005 Ohishi ........................... 378/8

FOREIGN PATENT DOCUMENTS

JP 2001-95790 4/2001

* cited by examiner

*Primary Examiner*—Craig E. Church
(74) *Attorney, Agent, or Firm*—Oblon, Spivak, McClelland, Maier & Neustadt, P.C.

(57) ABSTRACT

An X-ray diagnosis apparatus for obtaining an X-ray image comprises an X-ray radiator, a detector, a first mechanism, a second mechanism, a controller, and an image processor. The X-ray radiator is configured to radiate an X-ray to a specimen. The detector is configured to detect an X-ray data resulting from the X-ray. The first mechanism is coupled to the detector and is configured to shift the detector along a detecting plane of the detector. The second mechanism is coupled to the X-ray radiator and is configured to change a radiation direction of the X-ray against the detector. The controller is configured to control the second mechanism in accordance with the shift of the detector. The image processor is coupled to the detector and is configured to prepare a fluoroscopic image data as the X-ray image based on the X-ray data. The image processor also corrects a deformation of the fluoroscopic image data.

34 Claims, 12 Drawing Sheets

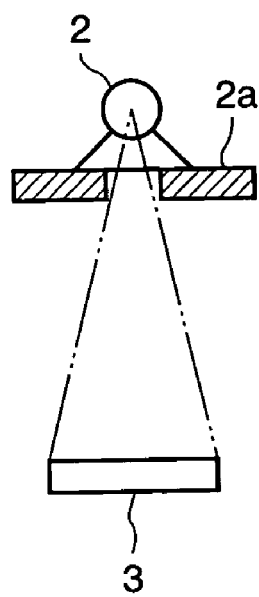
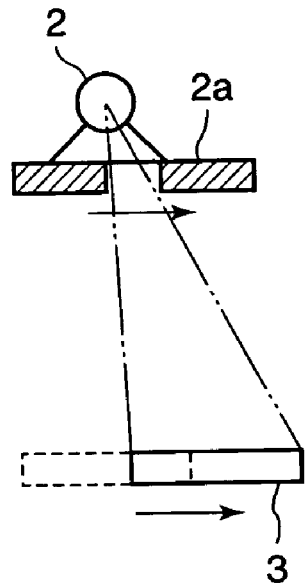
FIG. 3A  FIG. 3B
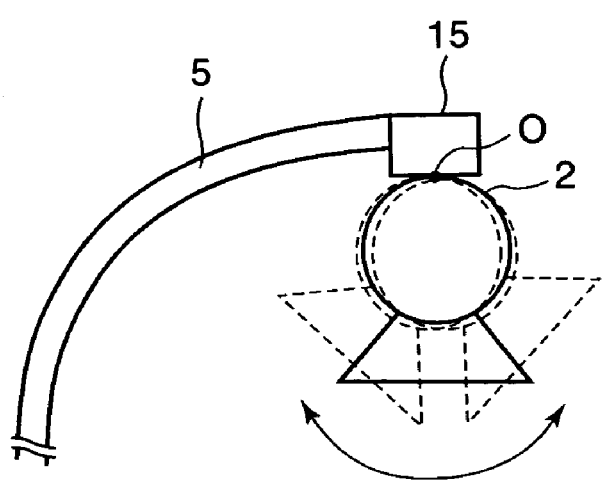
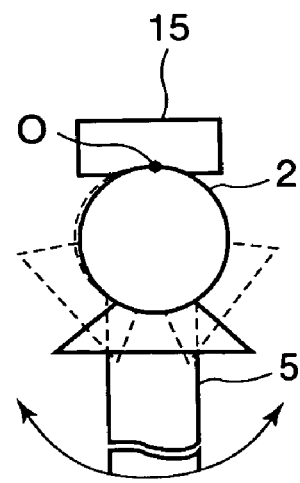
FIG. 4A  FIG. 4B

X-RAY DIAGNOSIS APPARATUS

CROSS-REFERENCE TO RELATED APPLICATION

This application is based upon and claims the benefit of priority from prior Japanese Patent Application No. P2002-274288, filed on Sep. 20, 2002, the entire contents of which are incorporated herein by reference.

FIELD OF THE INVENTION

The present invention relates to an X-ray diagnosis apparatus for obtaining images resulting from an X-ray radiation.

BACKGROUND OF THE INVENTION

An X-ray diagnosis apparatus is known as an apparatus which obtains images based on an X-ray fluoroscopy or an X-ray radiography and is used for a medical diagnosis. One type of the X-ray diagnosis apparatus is configured for a purpose of a therapy, an angiography examination, and/or the like. For example, such a type of the X-ray diagnosis apparatus is used for supporting a doctor to insert a thin guide-wire of a catheter or a device necessary for a therapy (hereinafter referred to as a device) into a blood vessel of a patient or an examination object (hereinafter referred to as a specimen) and further to pass the device through the blood vessel up to an affected part. The apparatus is also used for acquiring angiography images by injecting a contrast agent into a blood vessel of the specimen and fluoroscoping the specimen.

During an operation of passing the device up to the affected part as described above, the X-ray diagnosis apparatus radiates a weak X-ray to the specimen while the resulting fluoroscopic images are displayed in a dedicated display in real time. The doctor passes the device into the blood vessel by referring to the displayed fluoroscopic images. Alternatively, it is also usual that the doctor do the same by referring to radiographed images which are necessary for a device insertion or by referring to vessel images displayed in the display. The vessel images are obtained by temporarily injecting a little contrast agent into the specimen.

However, according to a conventional X-ray diagnosis apparatus, as the device proceeds in the vessel, a head of the device may be positioned out of a display range of the display, depending on a proceeding direction of the device and/or a size of an image field of view.

When the above situation has occurred, the doctor or a radiological technologist (hereinafter referred to as an operator) has to operate a diagnostic table where the specimen lies and/or an arm holding an X-ray tube and a detector, using an operation unit, so as to place the head of the device within the display range. Further, when the operator operates to move the diagnostic table and/or the arm, the operator also has to care about interferences with peripheral equipments. Such requirement of operations and cares are burdensome for the operator.

Particularly, the arm is very heavy due to holding the X-ray tube and the detector and accordingly has a powerful force of inertia. Thus, when the arm is operated, it is difficult to adjust the arm position appropriately which requires a subtle adjustment.

In practice, the diagnostic table is usually operated so that the head of the device falls within the display range. In the operation, the diagnostic table is moved back and forth, from side to side, and/or up and down while the arm is fixed. Obviously, when the diagnostic table moves, the specimen on the diagnostic table is also moved. This movement is often not comfortable but rather stressful for the specimen. In addition, it is necessary to pay attention to medical appliances, such as, for example, the device inserted in the specimen and a tube for an intravenous drip which is injected into the specimen, so as not to be pulled out. Further, the diagnostic table is usually moved manually by the operator. Therefore, when the specimen is heavy, it is a hard work for the operator.

BRIEF SUMMARY OF THE INVENTION

According to a first aspect of the present invention, there is provided an X-ray diagnosis apparatus for obtaining an X-ray image. The X-ray diagnosis apparatus includes an X-ray radiator, a detector, a first mechanism, a second mechanism, a controller, and an image processor. The X-ray radiator is configured to radiate an X-ray to a specimen. The detector is configured to detect an X-ray data resulting from the X-ray. The first mechanism is coupled to the detector and is configured to shift the detector along a detecting plane of the detector. The second mechanism is coupled to the X-ray radiator and is configured to change a radiation direction of the X-ray against the detector. The controller is configured to control the second mechanism in accordance with the shift of the detector. The image processor is coupled to the detector and is configured to prepare a fluoroscopic image data as the X-ray image based on the X-ray data. The image processor also corrects a deformation of the fluoroscopic image data.

According to a second aspect of the present invention, there is provided an X-ray diagnosis apparatus for obtaining an X-ray image. The X-ray diagnosis apparatus includes an X-ray radiator, a detector, a first mechanism, a second mechanism, a controller, and an image processor. The X-ray radiator is configured to radiate an X-ray to a specimen. The detector is configured to detect an X-ray data resulting from the X-ray. The first mechanism is coupled to the detector and is configured to shift the detector along a detecting plane of the detector. The second mechanism is coupled to the X-ray radiator and is configured to cause the X-ray to be exposed throughout an effective detecting area of the detector. The controller is configured to control the second mechanism in accordance with the shift of the detector. The image processor is coupled to the detector and has a memory configured to store a past image data. The image processor is also configured to prepare a fluoroscopic image data based on the detected X-ray data and a reference image data, based on the past image data, of a part of the specimen similar to what is viewed in the fluoroscopic image data in accordance with the shift of the detector.

According to a third aspect of the present invention, there is provided an X-ray diagnosis apparatus for obtaining an X-ray image. The X-ray diagnosis apparatus comprises an X-ray radiator, a detector, a first mechanism, a second mechanism, a controller, a memory, an image processor, and display. The X-ray radiator is configured to radiate an X-ray to a specimen. The detector is configured to detect an X-ray data resulting from the X-ray. The first mechanism is coupled to the detector and is configured to shift the detector along a detecting plane of the detector. The second mechanism is coupled to the X-ray radiator and is configured to cause the X-ray to be exposed throughout an effective detecting area of the detector. The controller is configured to control the second mechanism in accordance with the shift of the first mechanism. The memory is configured to store one or more past fluoroscopic image data. The image processor is configured to prepare a fluoroscopic image data based on the detected X-ray data and a contrast-enhanced reference image data based on at least one of the past fluoroscopic image data. The image processor is further configured to perform a subtraction processing between the fluoroscopic image data and a part of the contrast-enhanced reference image data. The part is determined in accordance with the shift of the detector. The display is configured to display a subtraction processed image.

BRIEF DESCRIPTION OF THE DRAWINGS

A more complete appreciation of embodiments of the present invention and many of its attendant advantages will be readily obtained by reference to the following detailed description considered in connection with the accompanying drawings, in which:

FIG. 3A is an illustration showing an original relationship between an X-ray radiation and an X-ray detection according to the first embodiment of the present invention;

FIG. 3B is an illustration showing an exemplary adjusted relationship between an X-ray radiation and an X-ray detection according to the first embodiment of the present invention;

FIG. 4A is an illustration showing an exemplary movement of an X-ray tube in a first direction according to the first embodiment of the present invention;

FIG. 4B is an illustration showing an exemplary movement of the X-ray tube in a second direction according to the first embodiment of the present invention;

DETAILED DESCRIPTION OF THE PREFERRED EMBODIMENTS

Embodiments of the present invention will be described with reference to the accompanying drawings.

(First Embodiment)

Figure 1:
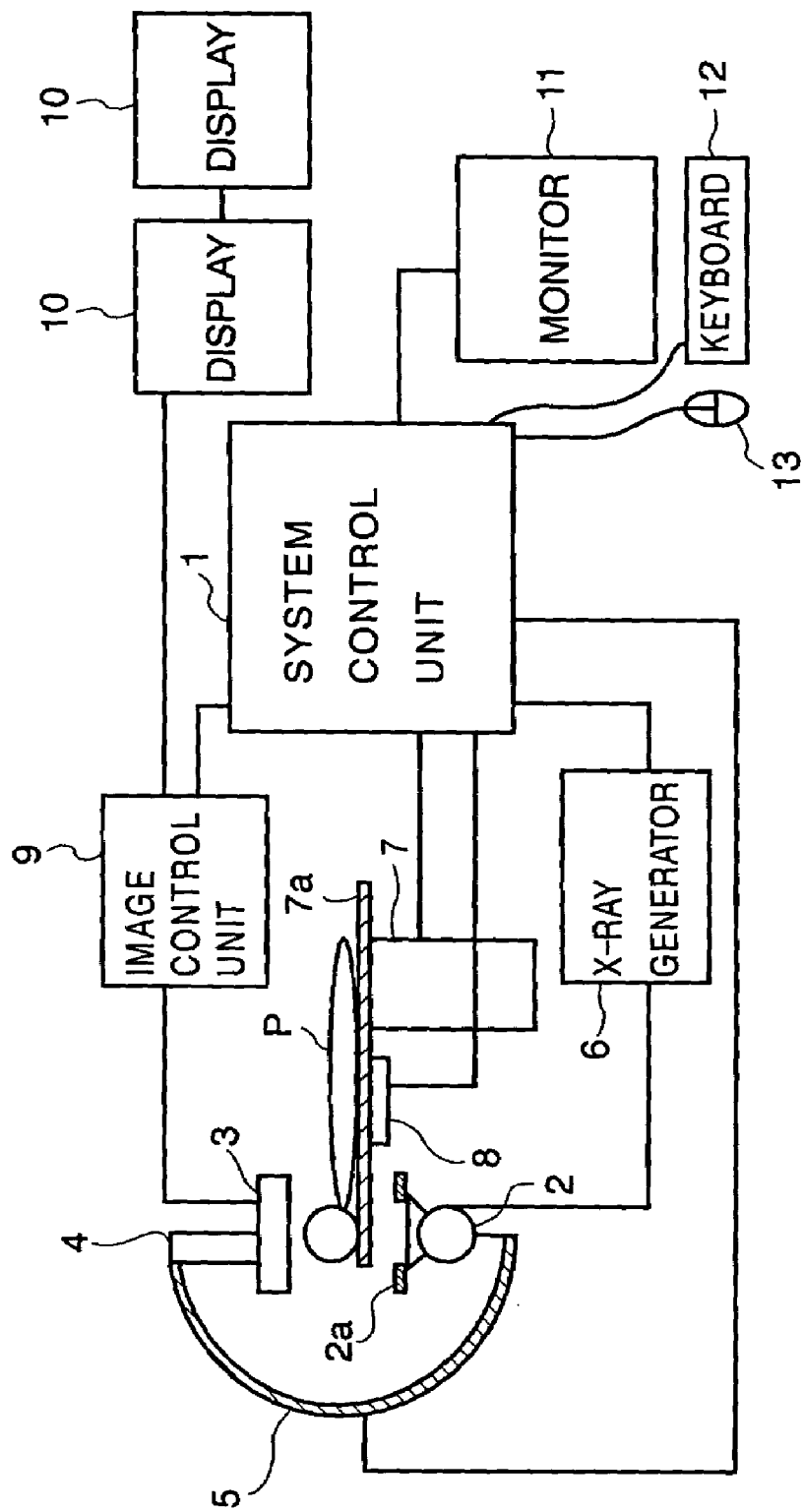
FIG. 1 is a block diagram showing an exemplary configuration of an X-ray diagnosis apparatus according to a first embodiment of the present invention.

FIG. 1 is a block diagram showing an exemplary configuration of an X-ray diagnosis apparatus according to a first embodiment of the present invention.

The X-ray diagnosis apparatus according to the first embodiment of the present invention includes a system control unit 1 which controls over the X-ray diagnosis apparatus, an X-ray tube 2 which radiates an X-ray, a detector 3 which detects the X-ray radiated from the X-ray tube 2, a detector supporter 4 which supports the detector 3, an arm 5 which supports the X-ray tube 2 and the detector 3 through the detector supporter 4, an X-ray generator 6 which supplies the X-ray tube 2 with power so that the X-ray tube 2 radiates an X-ray, a diagnostic table 7 where the specimen lies, an operation unit 8 which is used for operating the arm 5 and the diagnostic table 7, an image control unit 9 which prepares images based on X-ray information (or data) obtained from the detector 3 and further has a processor that performs various types of image processing, and displays 10 which display the prepared images or the processed images.

The X-ray tube 2 is equipped with a collimator 2a which controls a radiation direction and range (or field) of the X-ray radiated from the X-ray tube 2. Further, the system control unit 1 is connected to a monitor 11 exclusively used for the system control unit 1. The system control unit 1 is further connected to a user interface, such as a keyboard 12 and a mouse 13 which are used for operating GUIs (graphical user interfaces) displayed in the monitor 11. The system control unit 1 also controls to drive the arm 5 and the diagnostic table 7. In addition, the system control unit 1 controls the X-ray generator 6 so as to control an X-ray to be generated and also controls the image control unit 9, which manages image acquisition. Still further, the system control unit 1 manages data, such as specimen information, and also controls peripheral equipments, such as, for example, an injector and an imager.

Figure 2:
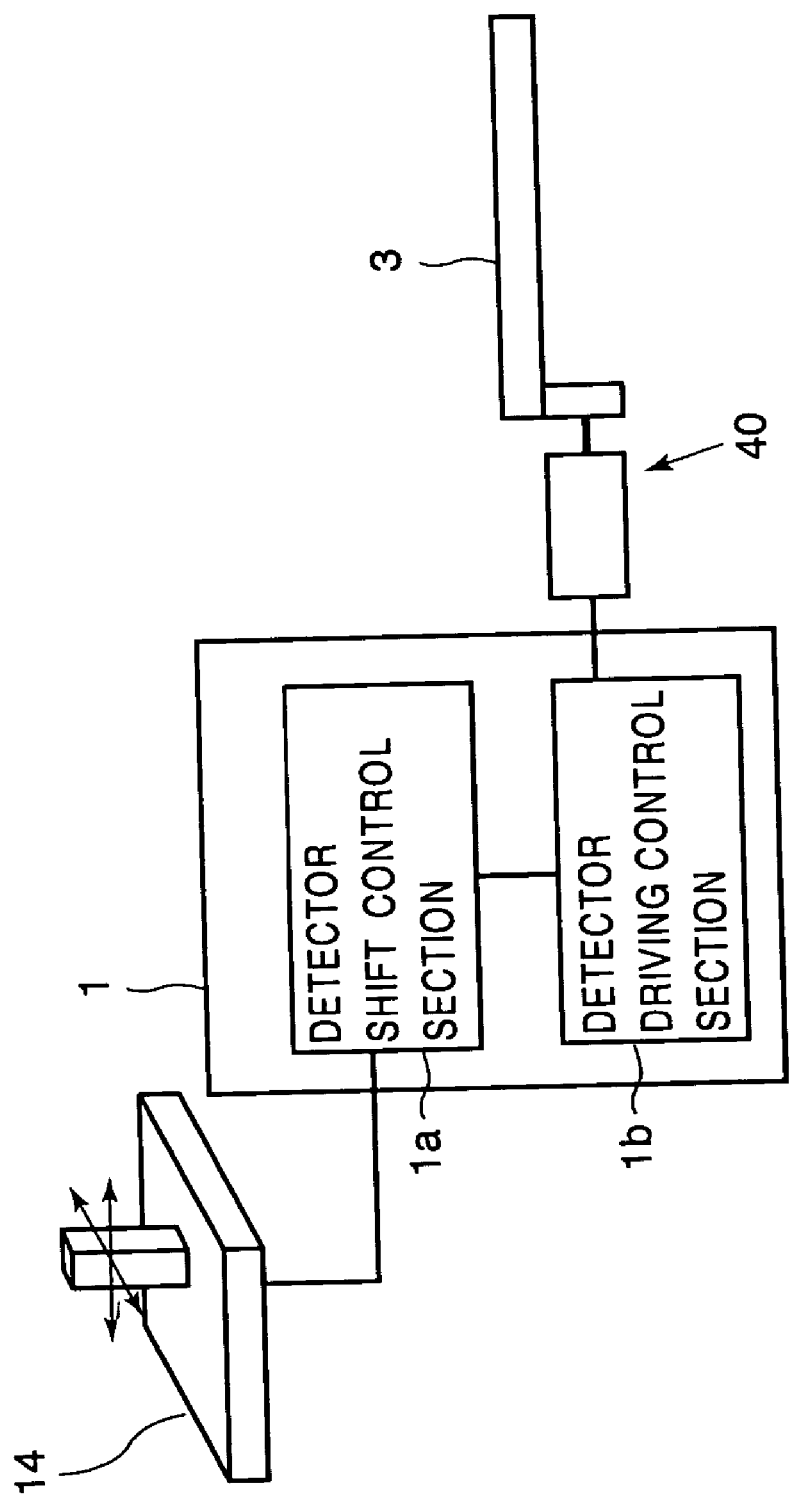
FIG. 2 is a block diagram for explaining an example of a parallel shift control of a detector according to the first embodiment of the present invention.

FIG. 2 is a block diagram for explaining an example of a parallel shift control of the detector 3 according to the first embodiment of the present invention. As shown in FIG. 2, the system control unit 1 includes a detector shift control section 1a and a detector driving control section 1b. The detector shift control section 1a controls the detector 3 to shift in parallel with a detection plane of the detector 3. The system control unit 1 is further connected to an operation lever 14. Information according to an operation of the operation lever 14 is provided to the detector shift control section 1a which accordingly determines a shift distance and direction of the detector 3. The determined distance and direction is transferred to the detector driving control section 1b from the detector shift control section 1a. The detector driving control section 1b controls a detector shift mechanism 40 to shift the detector 3 by the determined distance in the determined direction. The detector shift mechanism 40 is physically provided in between the detector 3 and the detector supporter 4. The detector shift mechanism 40 will be described in more detail later.

The detector driving control section 1b is capable of executing a plurality of controls necessary for driving the detector 3 simultaneously. The detector 3 is coupled with the detector shift mechanism 40 through gears, linear-movement type bearings, or the like. Accordingly, it is configured that a driving force by the detector shift mechanism 40 is transformed into a linear movement of the detector 3.

When the detector 3 is shifted in response to an operation of the operation lever 14, the X-ray tube 2 and the detector 3 are not faced to each other in alignment Due to such a misalignment, if the X-ray tube 2 is fixed as it is, an X-ray radiated from the X-ray tube 2 is only partially exposed to and detected by the detector 3 or not detected at all, in comparison with the detection before the detector 3 is shifted. This prevents from efficiently ensuring a field of view in resulting images. Therefore, it is helpful to adjust the radiation field and direction of the X-ray radiated from the X-ray tube 2 in accordance with the shift of the detector 3.

In the X-ray diagnosis apparatus according to the first embodiment of the present invention, an X-ray radiation by the X-ray tube 2 is adjusted as shown in FIGS. 3A and 3B. FIG. 3A is an illustration showing an original relationship between an X-ray radiation and an X-ray detection according to the first embodiment of the present invention. Further, FIG. 3B is an illustration showing an exemplary adjusted relationship between an X-ray radiation and an X-ray detection according to the first embodiment of the present invention.

As shown in FIG. 3B, the collimator 2a is configured that its position and aperture are adjustable in conjunction with the shift of the detector 3. Such a configuration shown in FIG. 3B will be described in detail later. Although it may be necessary to widen a radiation angle of the X-ray tube 2, it is not necessary for the X-ray tube 2 to change a radiation direction. Therefore, by adjusting the collimator 2a's position and aperture in conjunction with the shift of the detector 3, it is possible to control an X-ray radiation field in conformity with the shift of the detector 3. In case that there are two or more collimators 2a for the X-ray tube 2 (in other words, collimators 2a in two or more layers), each of the collimators 2a may be independently controlled its position and aperture so that a collimated X-ray is efficiently exposed to a predetermined detection area of the detector 3 through the specimen.

Alternatively, the X-ray tube 2 may be controlled as shown in FIGS. 4A and 4B when the detector 3 is shifted. FIG. 4A is an illustration showing an exemplary movement of the X-ray tube 2 in a first direction according to the first embodiment of the present invention. Also FIG. 4B is an illustration showing an exemplary movement of the X-ray tube 2 in a second direction according to the first embodiment of the present invention.

An X-ray tube supporter 15 which supports the X-ray tube 2 is connected to the arm 5 and is configured to be capable of adjusting a radiation direction by the X-ray tube 2 around a mounting point O where the X-ray tube 2 is mounted on the X-ray tube supporter 15. As shown in dotted lines in FIGS. 4A and 4B, the X-ray tube supporter 15 has a pivot mechanism that makes it possible to tilt the X-ray tube 2 in two axes directions. The X-ray tube 2 is independently tilted in each or both of the two axes directions by the X-ray tube supporter 15 in conjunction with the shift of the detector 3. According to such a configuration, it may be possible to always allocate an X-ray radiation field on an effective detecting area of the detector 3, by adjusting a radiation direction of the X-ray tube 2 in conjunction with the shift of the detector 3.

Figure 5:
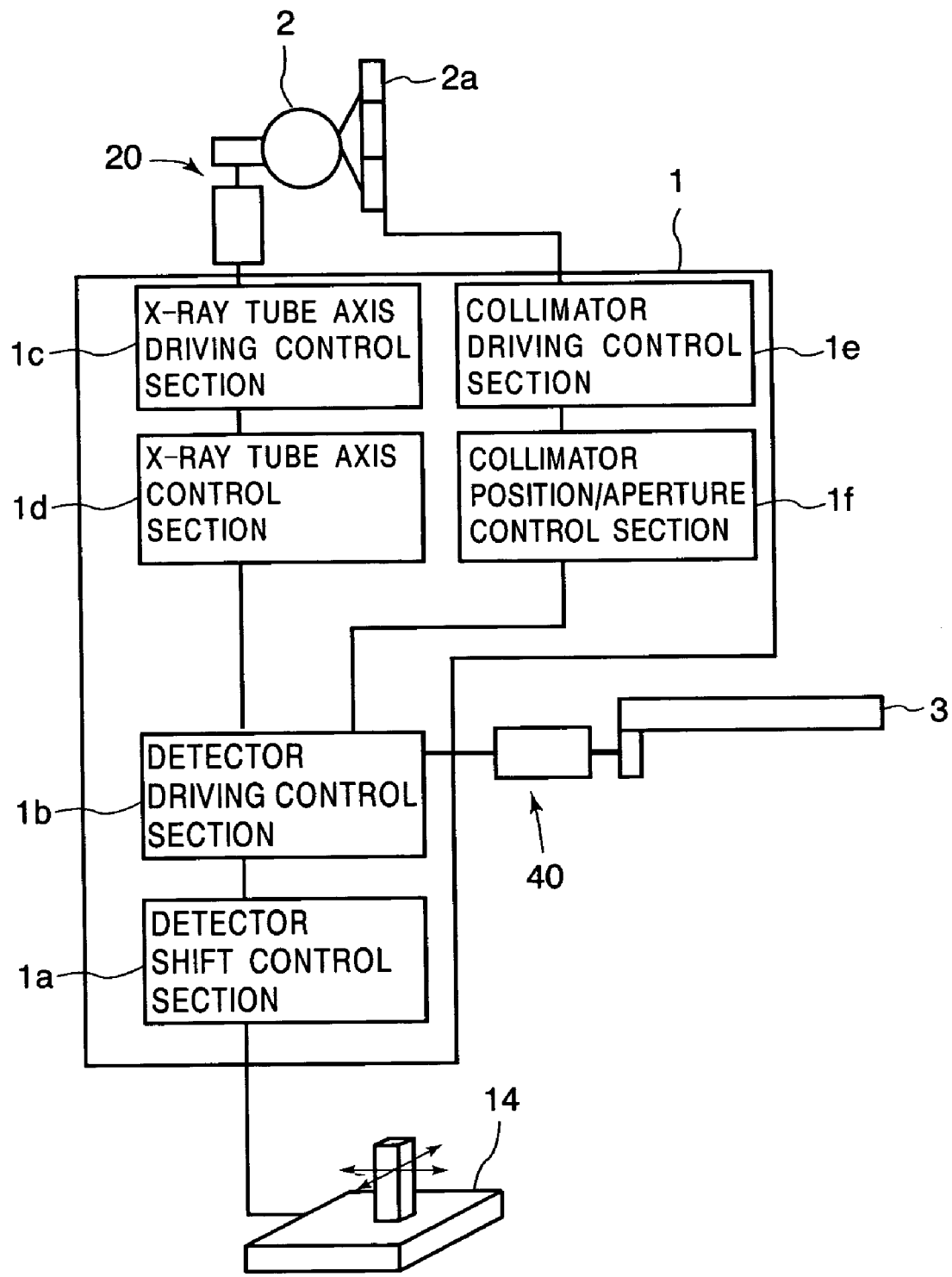
FIG. 5 is a block diagram showing an exemplary configuration of a system control unit for explaining a control regarding a position of a collimator and a radiation direction adjustment of the X-ray tube according to the first embodiment of the present invention.

FIG. 5 is a block diagram showing an exemplary configuration of the system control unit 1 for explaining a control regarding a position of the collimator 2a and a radiation direction adjustment of the X-ray tube 2 which have been described above according to the first embodiment of the present invention. As shown in FIG. 5, the system control unit 1 further includes an X-ray tube axis driving control section 1c and an X-ray tube axis control section 1d which are used for adjusting a radiation direction of the X-ray tube 2. The system control unit 1 also includes a collimator driving control section 1e and a collimator position/aperture control section 1f which are used for adjusting a position and aperture of the collimator 2a. Each collimating member of the collimator 2a may be controlled independently.

When the operation lever 14 is operated, operation information is provided to the detector shift control section 1a. This detector shift control section 1a determines in which direction and how much the detector 3 is shifted. Information regarding the distance and the direction is sent to the detector driving control section 1b from the detector shift control section 1a. The detector driving control section 1b controls the detector shift mechanism 40 to shift the detector 3 by a predetermined distance in a predetermined direction based on the determined distance and the determined direction.

The operation information in response to the operation lever 14's operation is also sent to the X-ray tube axis control section 1d from the detector driving control section 1b. The X-ray tube axis control section 1d determines in which direction and how much the X-ray tube 2 is moved (or rotated). Information regarding the amount and the direction is sent to the X-ray tube axis driving control section 1c from the X-ray tube axis control section 1d. The X-ray tube axis driving control section 1c controls an X-ray tube moving mechanism 20 to move (rotate) the X-ray tube 2 by a predetermined amount in a predetermined direction based on the determined amount and the determined direction. The X-ray tube moving mechanism 20 may include gears, rotational movement type bearings, and/or the like.

Further, the operation information in response to the operation lever 14's operation is still also sent to the collimator position/aperture control section 1f from the detector driving control section 1b. The collimator position/aperture control section 1f determines a new position and aperture of the collimator 2a. Information regarding the new position and aperture is sent to the collimator driving control section 1e from the collimator position/aperture control section 1f. The collimator driving control section 1e controls the collimator 2a to move by a predetermined amount to be placed at the determined position. The collimator driving control section 1e further controls the collimator 2a to adjust its aperture based on the determined aperture.

Figure 6A:
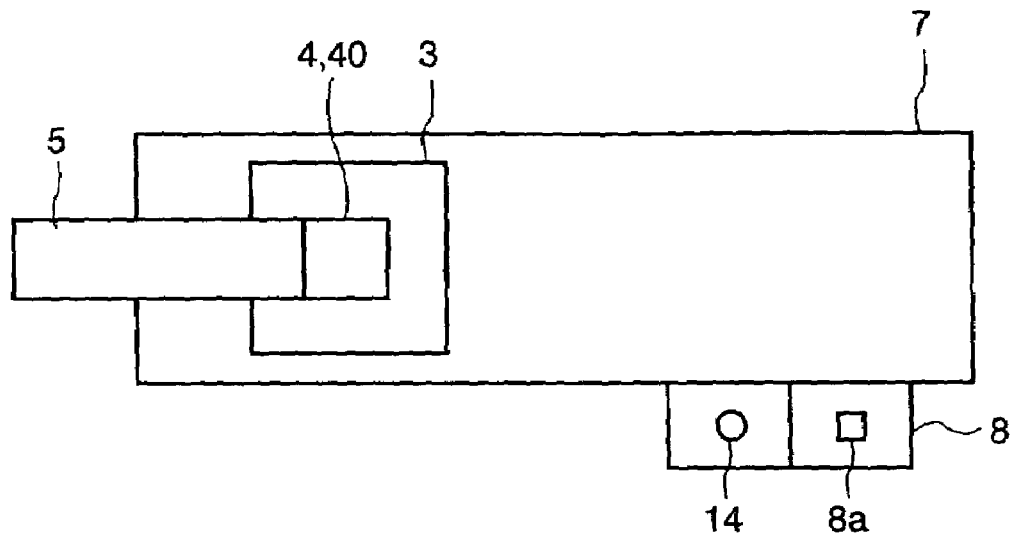
FIG. 6A is an illustration showing an original position of the detector according to the first embodiment of the present invention.
Figure 6B:
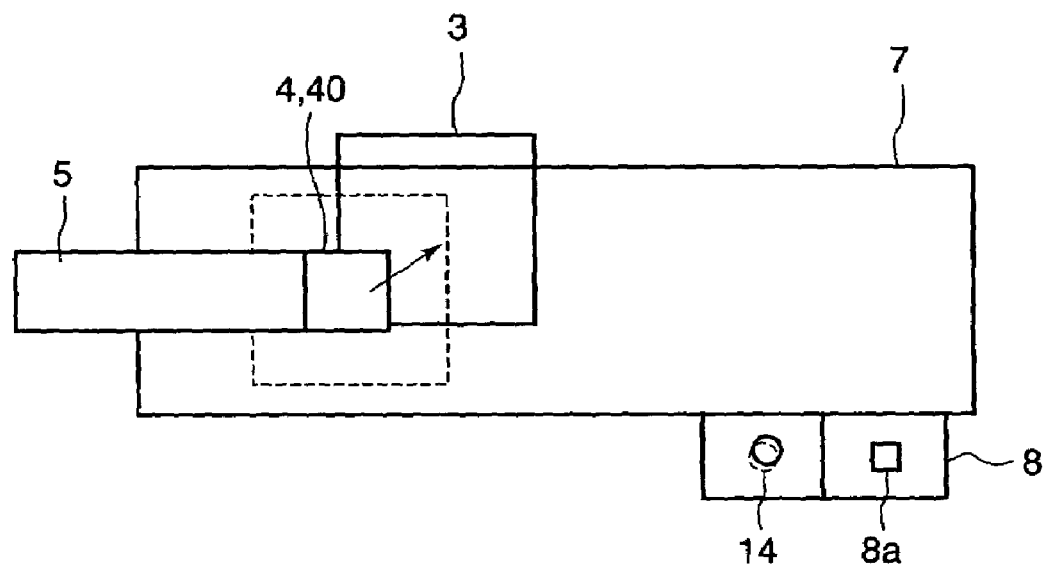
FIG. 6B is an illustration showing an exemplary position of the detector shifted based on an operation lever's operation according to the first embodiment of the present invention.

FIG. 6A is an illustration showing an original position of the detector 3 according to the first embodiment of the present invention. Also FIG. 6B is an illustration showing an exemplary position of the detector 3 shifted based on the operation lever 14's operation according to the first embodiment of the present invention. Each of FIGS. 6A and 6B shows a view of the X-ray diagnosis apparatus from the above of the diagnostic table 7.

As described before, by operating the operation lever 14, the detector 3 is shifted to a desired (or appropriate) position without moving the arm 5 and the diagnostic table 7. The detector 3 is supported by the detector supporter 4 which is provided at the arm 5, and is configured to be capable of shifting in parallel with the detection plane of the detector 3 in accordance with the detector shift mechanism 40. Therefore, when the operation lever 14 is operated by a given amount towards an upper right direction in FIG. 6B, the detector 3 is shifted by a predetermined distance based on the given operated amount in substantially the same direction as the operation lever 14's operation as shown in FIG. 6B.

Further, in conjunction with the shift of the detector 3, and following the controls in the system control unit 1 described with FIG. 5 before, radiation direction of the X-ray tube 2 is also adjusted and the collimator 2a is shifted to an appropriate position with an appropriate aperture so that an X-ray radiated from the X-ray tube 2 appropriately enters (or is exposed to) the detector 3 after shifted.

Still further, the shifted detector 3 is automatically returned to the original position (a home position) by operating (or pressing, for example) home position switch 8a provided in the operation unit 8. Here, the home position may be a default (or initially determined) position of the detector supporter 4 and the detector 3. The home position may be set up when the X-ray diagnosis apparatus is installed in a facility. Alternatively, the home position may be set up at the time of shipment of the X-ray diagnosis apparatus from a manufacturing plant, for example. Any other possible time may be applicable to the set-up of the home position.

Figure 7:
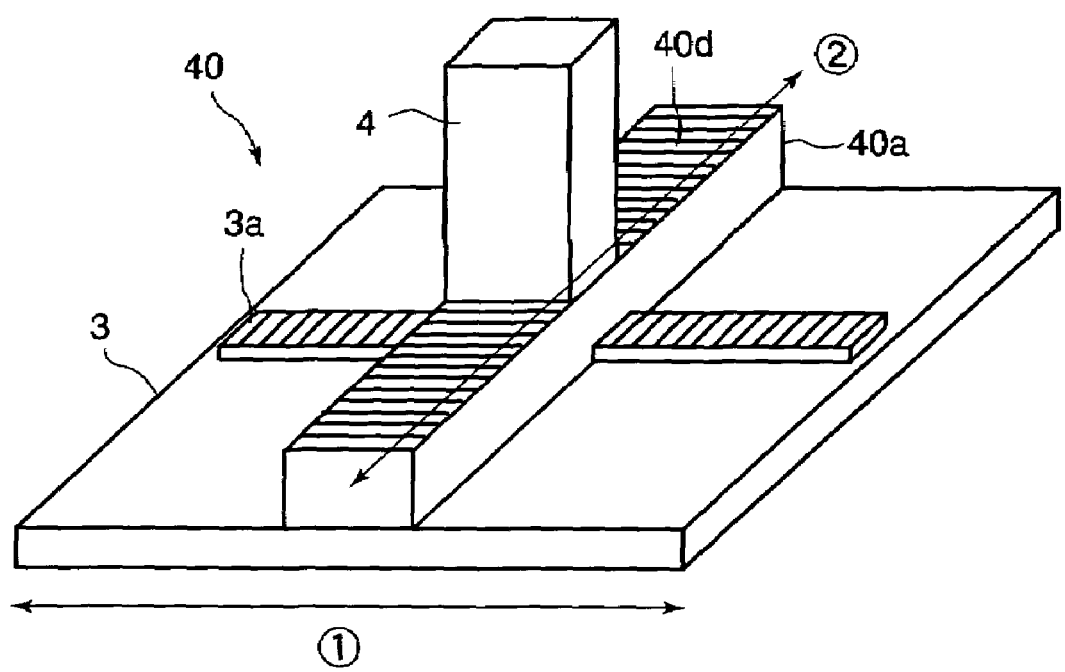
FIG. 7 is an illustration showing an exemplary configuration of a detector shift mechanism according to the first embodiment of the present invention.
Figure 8A:
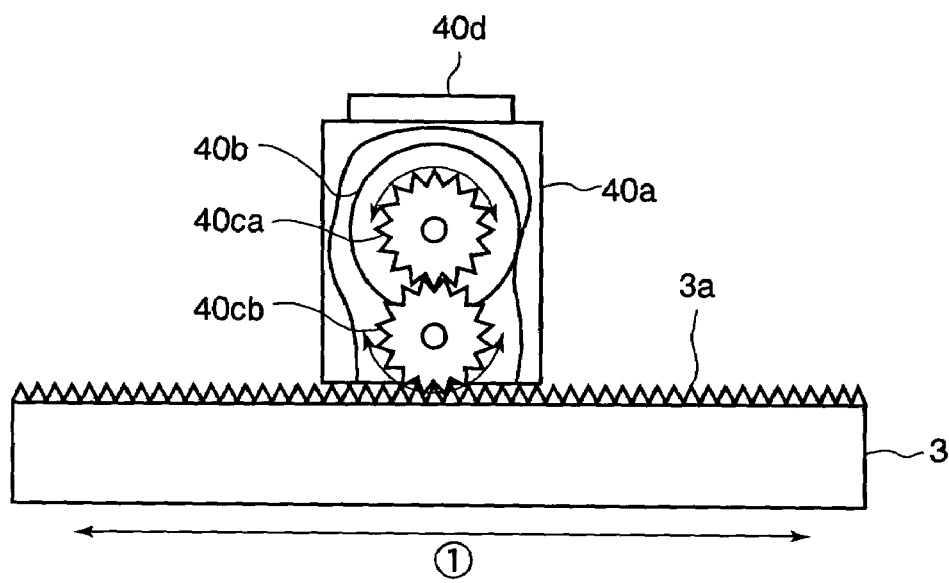
FIG. 8A is an illustration showing an example of a first detailed configuration of the detector shift mechanism shown in FIG. 7 according to the first embodiment of the present invention.
Figure 8B:
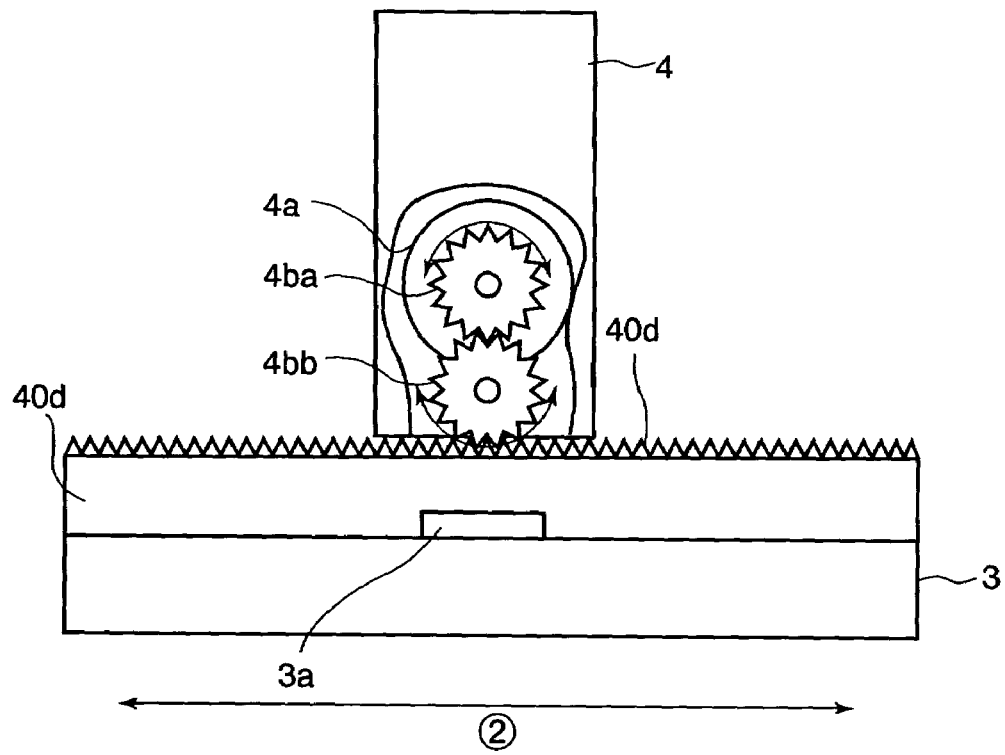
FIG. 8B is an illustration showing an example of a second detailed configuration of the detector shift mechanism shown in FIG. 7 according to the first embodiment of the present invention.

The detector shift mechanism 40 mentioned before will be described in detail with reference to FIGS. 7, 8A, and 8B. FIG. 7 is an illustration showing an exemplary configuration of a detector shift mechanism according to the first embodiment of the present invention. In addition, FIG. 8A is an illustration showing an example of a first detailed configuration of the detector shift mechanism shown in FIG. 7 according to the first embodiment of the present invention. Further, FIG. 8B is an illustration showing an example of a second detailed configuration of the detector shift mechanism shown in FIG. 7 according to the first embodiment of the present invention.

As shown in FIG. 7, the detector shift mechanism 40 has a mechanism which allows the detector supporter 4 to move along two mutually orthogonal axes (axis ①, axis ②). The detector supporter 4 can move independently along one axis and the other, respectively. In other words, since the detector supporter 4 is fixed at the arm 5, this configuration means that the detector shift mechanism 40 allows the detector 3 to move along each of the two axes, independently. Movement (or shift) along the respective axes is determined by calculating a distance and a direction based on the operation lever 14's operation as described before. The detector shift mechanism 40 includes a detector backside gear 3a, a mobile unit 40a, a mobile unit backside gear 40d, and a motor (not shown in FIG. 7) which are controlled based on the calculated distance and the calculated direction so as to move the detector 3 along the respective axes. The detector backside gear 3a, the mobile unit 40a, the mobile unit backside gear 40d, the motor, and the like included in the detector shift mechanism 40 will be described in detail below.

Movement along the axis ① in FIG. 7 means a slide of the mobile unit 40a on the detector backside gear 3a. As shown in FIG. 8A, the detector shift mechanism 40 includes the detector backside gear 3a which is provided on the backside of the detector 3, the mobile unit 40a which moves on the detector backside gear 3a, and the mobile unit backside gear 40d which is provided on the backside of the mobile unit 40a. In the mobile unit 40a, there are a motor 40b and a gear 40ca which is rotated by the motor 40b. The mobile unit 40a further includes a gear 40cb which is engaged with the gear 40ca and is accordingly rotated when the gear 40ca is rotated. The gear 40cb is further engaged with the detector backside gear 3a. Therefore, when the gear 40cb is rotated, the mobile unit 40a slides on the detector backside gear 3a. That is, the detector 3 moves against the mobile unit 40a along the axis ①. A power supply line for driving the motor 40b may be wired to the motor 40b from the system control unit 1 through the arm 5 and the detector supporter 4. Control lines for controlling the motor 40b may also be wired in a similar manner.

Movement along the axis ② in FIG. 7 means a slide of the detector supporter 4 on the mobile unit backside gear 40d. As shown in FIG. 8B, the detector shift mechanism 40 further includes the mobile unit backside gear 40d which is provided on the backside of the mobile unit 40a. In the detector supporter 4, there are a motor 4a and a gear 4ba, which is rotated by the motor 4a. The detector supporter 4 further includes a gear 4bb which is engaged with the gear 4ba and is accordingly rotated when the gear 4a is rotated. The gear 4bb is further engaged with the mobile unit backside gear 40d. Therefore, when the gear 4bb is rotated, the detector supporter 4 slides on the mobile unit backside gear 40d. That is, the detector 3 engaged with the mobile unit 40a moves against the detector supporter 4 along the axis ②. A power supply line for driving the motor 4a may be wired to the motor 4a from the system control unit 1 through the arm 5 and the detector supporter 4. Control lines for controlling the motor 4a may also be wired in a similar manner.

As shown in FIGS. 8A and 8B, by independently driving each of the motors 40b and 4a, it becomes possible to shift the detector 3 in parallel with its detection plane in any direction including an oblique direction (as a result of the shift). According to the configurations shown in FIGS. 8A and 8B, the detector 3 is allowed to shift within a range of the size of the detector 3. However, if it is possible to make the detector backside gear 3a and/or the mobile unit backside gear 40d longer, the detector 3 can accordingly be shifted beyond the size of the detector 3. A position relationship between the mobile unit 40a and the detector supporter 4 is governed, for example, by a guide for a linear movement, such as the mobile unit backside gear 40d, or the like. Accordingly, a parallel movement (shift) can be realized between the mobile unit 40a and the detector supporter 4. Also a position relationship between the mobile unit 40a and the detector 3 is similarly governed, for example, by a guide for a linear movement, such as the detector backside gear 3a, or the like. Accordingly, a parallel movement (shift) can be realized between the mobile unit 40a and the detector 3.

(Second Embodiment)

Figure 9A:
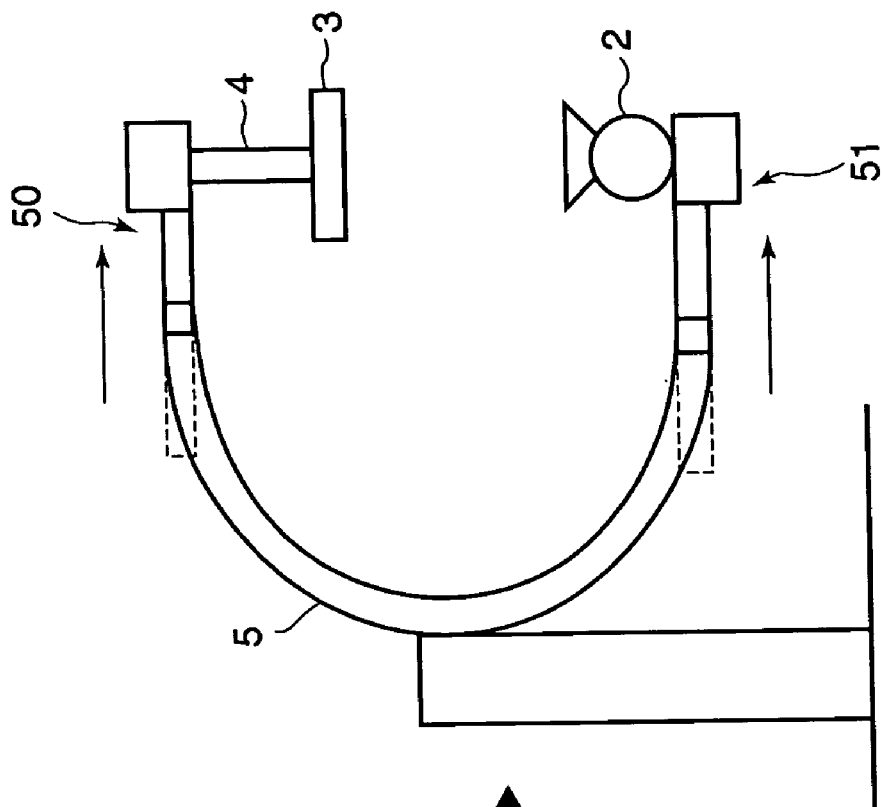
FIG. 9A is an illustration showing a exemplary configuration of an X-ray diagnosis apparatus in an original position status according to a second embodiment of the present invention.
Figure 9B:
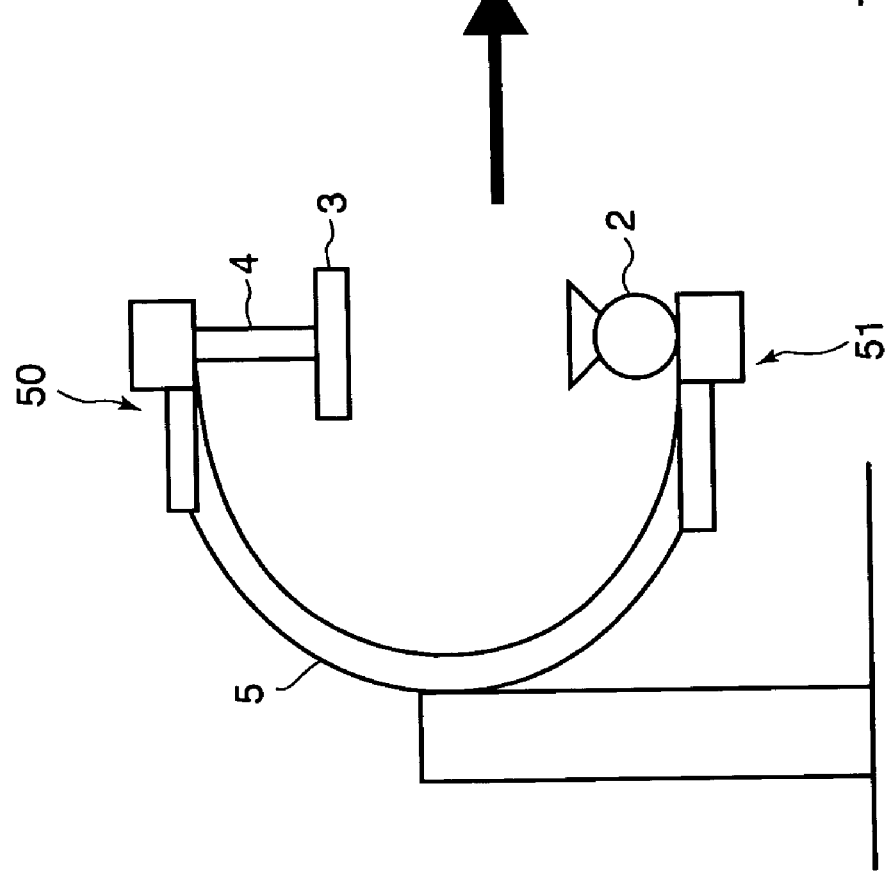
FIG. 9B is an illustration showing a exemplary configuration of the X-ray diagnosis apparatus in an extended position status according to the second embodiment of the present invention.

FIGS. 9A and 9B are illustrations showing an exemplary configuration of an X-ray diagnosis apparatus according to a second embodiment of the present invention. In the second embodiment, components similar to those described in the first embodiment will be given the same references and such references will be cited as described in the first embodiment although the references are not all shown in FIGS. 9A and 9B. A detailed explanation for those will be omitted below.

The X-ray diagnosis apparatus according to the second embodiment includes an extension mechanism 50 which is provided at the arm 5 and coupled with the detector supporter 4. The extension mechanism 50 is configured to move in parallel with the detection plane of the detector 3. For example, the extension mechanism 50 may move towards the arm 5 and also move away from the arm 5. Therefore, since the detector 3 is connected to the detector supporter 4 through the detector shift mechanism 40, a position of the detector 3 can further be shifted in parallel with the detection plane of the detector 3 in combination with the detector shift mechanism 40.

The X-ray diagnosis apparatus also includes an extension mechanism 51 which is provided at the arm 5 and coupled with the X-ray tube supporter 15. The extension mechanism 51 is configured to move in parallel with the detection plane of the detector 3. For example, the extension mechanism 51 may move towards the arm 5 and also move away from the arm 5 as similar to the extension mechanism 50. Therefore, since the X-ray tube 2 is connected to the X-ray tube supporter 15 through the X-ray tube moving mechanism 20, a position of the X-ray tube 2 can also be shifted in parallel with the detection plane of the detector 3 in conjunction with the shift of the detector 3. In such a configuration, when the operator continues to operate the operation lever 14 so as to shift the detector 3, the detector 3 is shifted to an extent limited by the detector shift mechanism 40 in a manner described in the first embodiment. If the operator further continues to operate the operation lever 14, the operation of the detector shift mechanism 40 is automatically switched to an operation of the extension mechanism 50. In accordance with the operation of the operation lever 14, the extension mechanism 50 is moved to shift a position of the detector 3. When the extension mechanism 50 is moved, the extension mechanism 51 is also moved by the same distance in the same direction as the extension mechanism 50 in conjunction with the extension mechanism 50. Accordingly, a position relationship between the detector 3 and the X-ray tube 2 is substantially always kept constant. Further, since a shift range of the detector 3 is expanded, it becomes possible to accommodate a wide range of X-ray fluoroscopy or radiography.

In the second embodiment of the present invention, the extension mechanisms 50 and 51 are supported by the arm 5 and are driven by motors (not shown in FIGS. 9A and 9B). In addition, the X-ray diagnosis apparatus may include a lever which is independently provided for specifically operating the extension mechanisms 50 and 51. In this case, there may also be provided a home position switch or the like, which is used for automatically returning the extension mechanisms 50 and 51 to home positions initially determined, such as, for example, fixed positions of the detector 3 and the X-ray tube 2 described in the first embodiment.

Figure 10A:
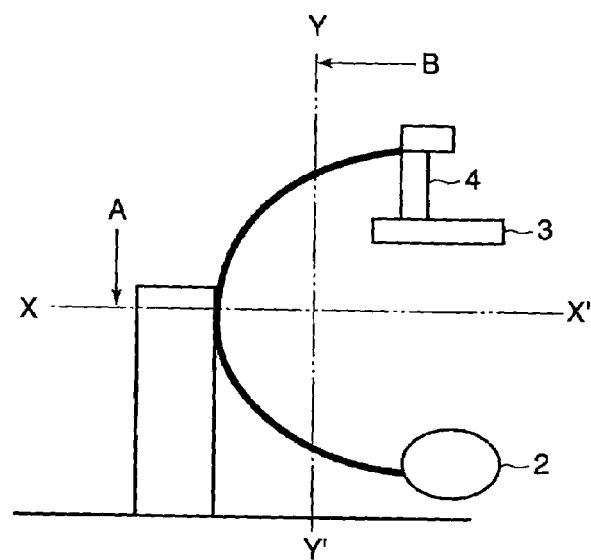
FIG. 10A is an illustration showing the X-ray diagnosis apparatus when extension mechanisms are at home positions according to the second embodiment of the present invention.
Figure 10B:
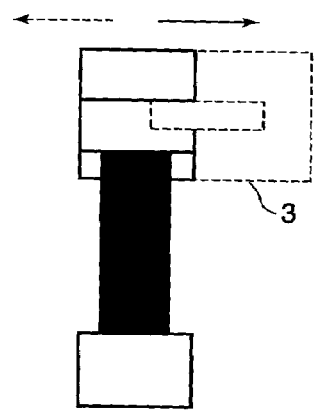
FIG. 10B is an illustration showing a first cross sectional view of the X-ray diagnosis apparatus according to the second embodiment of the present invention.
Figure 10C:
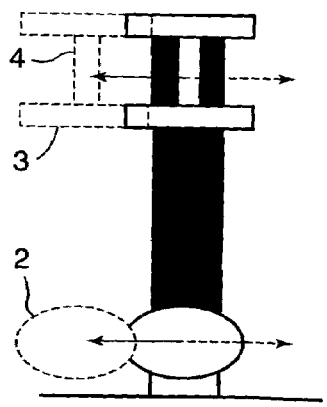
FIG. 10C is an illustration showing a second cross sectional view of the X-ray diagnosis apparatus according to the second embodiment of the present invention.

The extension mechanisms 50 and 51 may also be configured to move in a direction perpendicular to the direction shown in FIG. 9B. FIGS. 10A to 10C are illustrations showing another exemplary configuration of the X-ray diagnosis apparatus according to the second embodiment of the present invention. FIG. 10A is an illustration showing the X-ray diagnosis apparatus when the extension mechanisms 50 and 51 are at the home (or original) positions according to the second embodiment of the present invention. FIG. 10B is an illustration showing a cross sectional view of the X-ray diagnosis apparatus when it is viewed from a line X–X' shown in FIG. 10A according to the second embodiment of the present invention. Further, FIG. 10C is an illustration showing a cross sectional view of the X-ray diagnosis apparatus when it is viewed from a line Y–Y' shown in FIG. 10A according to the second embodiment of the present invention.

As shown in FIG. 10B, the extension mechanism 50 at the home (or original) position shown in FIG. 10A is capable of moving the detector supporter 4 coupled with the detector 3 in a direction perpendicular to the direction shown in FIG. 9B. Further, the extension mechanism 51 is also capable of moving the X-ray tube supporter 15 coupled with the X-ray tube 2 in the direction as described with FIG. 10B in conjunction with the extension mechanism 50 as shown in FIG. 10C. In embodiments of the present invention, one direction is understood as a direction (+direction) and the opposite direction (−direction).

(Third Embodiment)

In the first (and the second) embodiment(s) described above, when the detector 3 is shifted by the detector shift mechanism 40, it requires the X-ray tube 2 to change its radiation direction and also the collimator 2a to change its position and its aperture so that the radiated X-ray is appropriately exposed to a detection area of the detector 3 through the specimen lying between the X-ray tube 2 and the detector 3. Images, however, prepared based on such detection by the image control unit 9 may be deformed as shown in FIG. 11B.

Figures 11A, 11B:
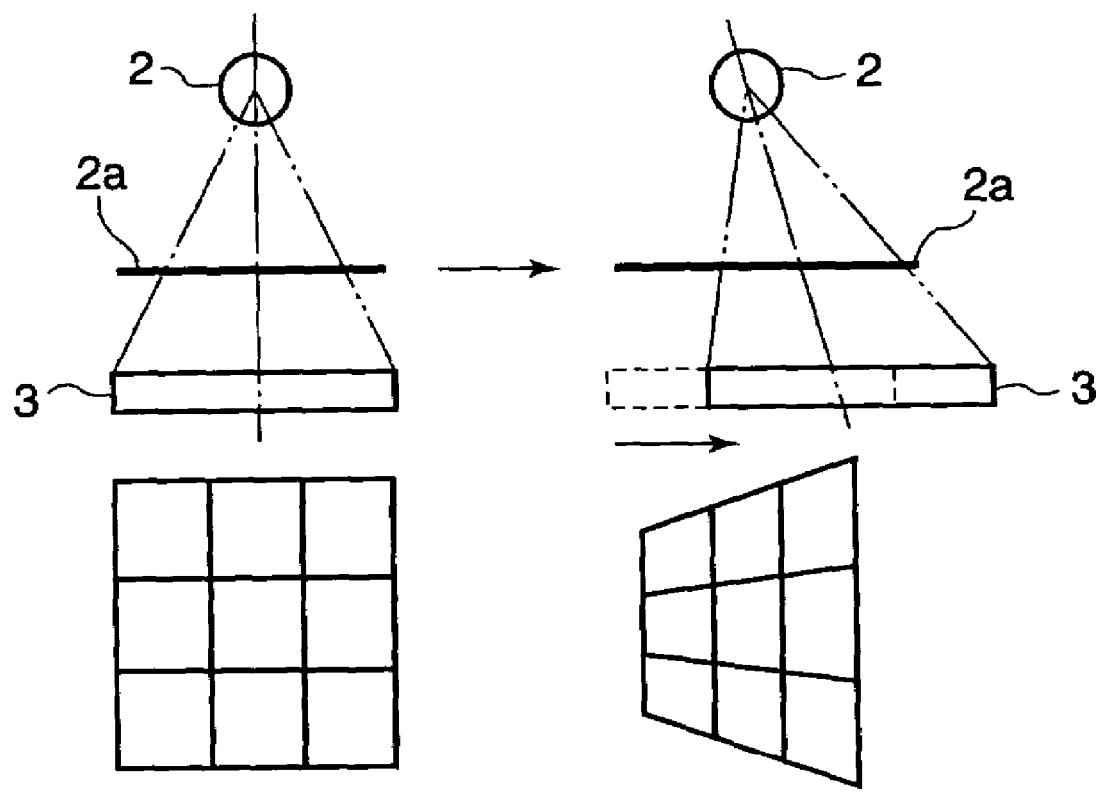
FIG. 11A is an illustration showing an X-ray detection and its resulting image at an original position according to a third embodiment of the present invention.
FIG. 11B is an illustration showing an X-ray detection and its resulting image at a shifted position according to the third embodiment of the present invention.

FIG. 11A is an illustration showing an X-ray detection and its resulting image at the home (or original) position according to a third embodiment of the present invention. FIG. 11B is an illustration showing an X-ray detection and its resulting image at the shifted position according to the third embodiment of the present invention.

In an exemplary image obtained when the detector 3 has been shifted, an image size (or width) of a part of the image obtained in a detection field of the detector 3 which is far from the X-ray tube 2 (to be precise, from an X-ray radiation focal point of the X-ray tube 2) becomes larger, compared to an image size (or width) of a part of the image obtained in a detection field of the detector 3 which is on an extension of the X-ray radiation focal point. On the other hand, an image size (or width) of a part of the image obtained in a detection field of the detector 3 which is near from the X-ray tube 2 (to be precise, from the X-ray radiation focal point of the X-ray tube 2) becomes smaller, compared to the image size (or width) of the part of the image obtained in the detection field of the detector 3 which is on the extension of the X-ray radiation focal point. Therefore, according to the third embodiment of the present invention, the X-ray diagnosis apparatus is configured to correct such a deformation in real time and to display a corrected image in the display 10.

Figure 12:
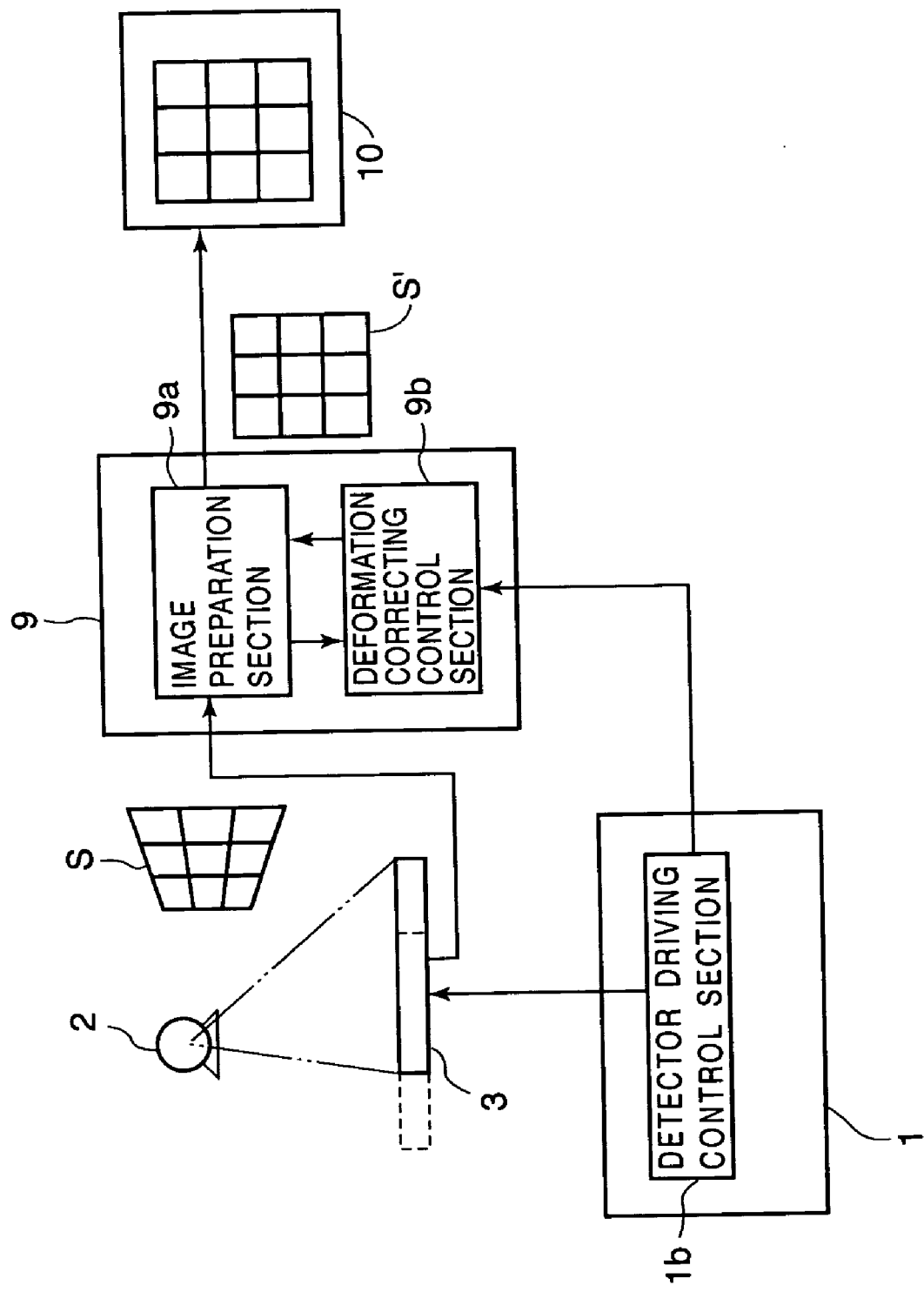
FIG. 12 is a block diagram showing an exemplary configuration of a system for correcting an image deformation according to a third embodiment of the present invention.

FIG. 12 is a block diagram showing an exemplary configuration of a system for correcting an image deformation according to the third embodiment of the present invention.

When the detector 3 is shifted, the detector driving control section 1b of the system control unit 1 provides a deformation correcting control section 9b of the image control unit 9 with information of the shifted distance and the shift direction of the detector 3. The deformation correcting control section 9b is also provided information of an image (i.e., a deformed image) S obtained in an image preparation section 9a of the image control unit 9. The deformation correcting control section 9b processes a deformation correction which is most appropriate for the image S based on the information of the shifted distance and the shift direction of the detector 3 provided from the detector driving control section 1b of the system control unit 1.

Such an appropriate deformation correcting processing may use a so-called trapezoidal deformation correcting processing which is generally implemented in a projector and the like. In concrete terms, the deformation correcting control section 9b corrects the deformation by converting each pixel position of pixels included in a deformed part of the image S to each pixel position of corresponding pixels included in an image which would be obtained if the detector 3 was not shifted.

Further, since a distance between the X-ray radiation focal point of the X-ray tube 2 and each pixel of the detector 3 (or a distance between the focal point and the specimen or the like) along a beam of the X-ray radiation becomes different from each other, even when it is a same-size object, such a same-size object is imaged in different sizes according to the distance.

For correcting such a deformation, a geometric expansion ratio is calculated based on a distance between the focal point and a specific part of the specimen along the X-ray beam and a distance between the focal point and a specific pixel where the X-ray through the specific art of the specimen is exposed. Using the geometric expansion rate calculated for each pixel of the detector 3, the correction can be made so as to obtain an image similar to an image to be obtained when the focal point of the X-ray tube 2 and the detector 3 are normally (or in alignment) faced to each other.

An example of such correction techniques is described in the U.S. Pat. No. 6,196,715 and is applicable to embodiments of the present invention.

Information of a corrected image S' based on the above correction is provided to the image preparation section 9a. The corrected image S', is implemented a normal image processing, such as a gray scale processing, a digital filtering processing, and the like, and is then displayed in the display 10. The above processing may be implemented in real time even during the fluoroscopy.

(Fourth Embodiment)

Figure 13:
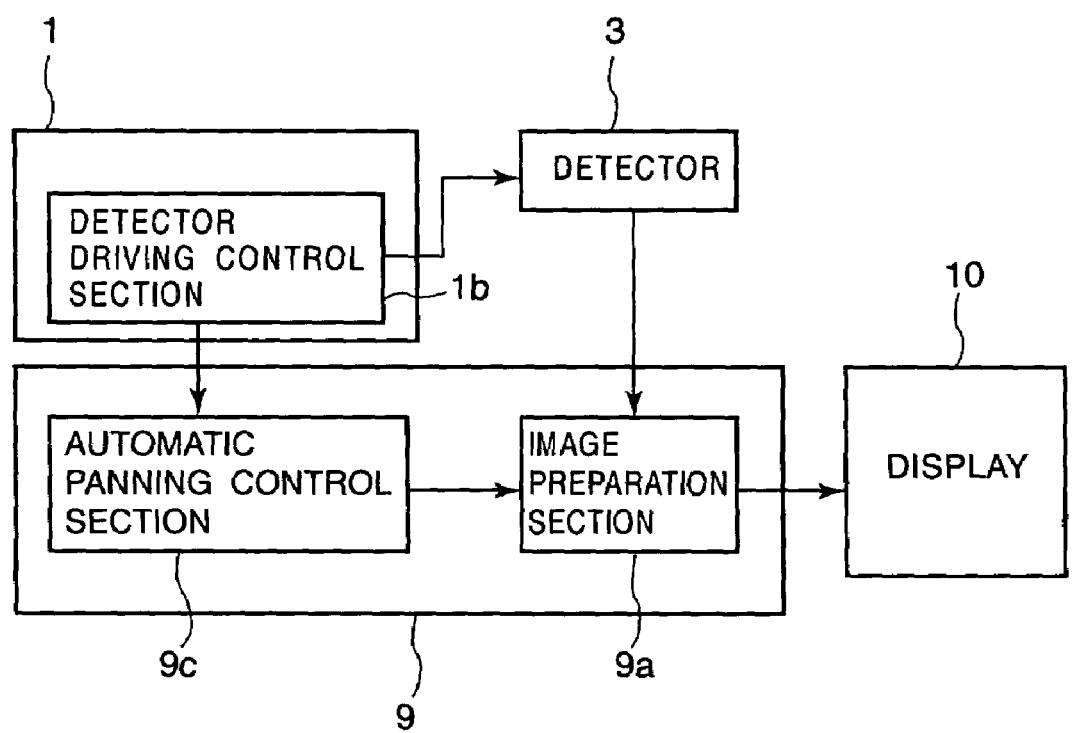
FIG. 13 is a block diagram showing an exemplary configuration of a system regarding an automatic panning of a reference image according to a fourth embodiment of the present invention.

FIG. 13 is a block diagram showing an exemplary configuration of a system regarding an automatic panning of a reference image according to a fourth embodiment of the present invention.

It is general that already obtained images are reproduced (or displayed) as reference images in the display 10 provided in an examination room while fluoroscopic images or radiographic images are displayed in real time in the display 10. It is also general that still images are produced based on the reproduced images and displayed as reference images in the display 10 while fluoroscopic images or radiographic images are displayed in real time in the display 10. The reference images may be referred for proceeding with medical examinations.

In practice, a group of radiographic images or a group of produced still images is displayed in a catalog form so as for the operator to select appropriate reference images (reproduced images or still images). Alternatively, the radiographic images or the produced still images are switched and displayed one by one in turn. Images to be selected as the reference images may usually be images radiographed at a position similar to a position where a predetermined image field of view is recognized in the fluoroscopy.

In the above case, however, according to embodiments of the present invention, the shift of the detector 3 results in changing an image field of view. Further, the image field of view is also changed when the operator moves a table top 7a of the diagnostic table 7, the arm 5, and/or the like. Consequently, a center of reference images already displayed in the display 10 becomes inconsistent with a center of an image field of view of images being obtained in the fluoroscopy. Therefore, the operator has to perform manual operations for matching the center of the displayed reference images with the center of the image field of view of images being obtained in the fluoroscopy.

The X-ray diagnosis apparatus according to the fourth embodiment of the present invention is configured to automatically match the center of the reference images with the center of the image field of view of images being obtained in the fluoroscopy by automatically making the reference images to be displayed to follow the shift of the detector 3 in conjunction with the shift of the detector 3.

As shown in FIG. 13, when the detector 3 is shifted, information of the shifted distance and the shift direction is provided to an automatic panning control section 9c of the image control unit 9 from the detector driving control section 1b of the system control unit 1. The automatic panning control section 9c converts the information into shift amounts of coordinates at a center of a predetermined image of the reference images as information regarding a shift amount and a shift direction of the reference images. The image preparation section 9a automatically shifts the reference images to a position based on the conversion result. The shifted reference images are displayed in the display 10 in real time.

Using the X-ray diagnosis apparatus according to the fourth embodiment, it is also possible, for example, to automatically make a reference mask image to follow fluoroscopic images being obtained in real time. The reference mask image is used as a road map while the doctor inserts the device into the specimen during the fluoroscopy.

Procedures for preparing the reference mask image will be described below. First of all, the operator operates the operation unit 8 so as to select a function of preparing a fluoroscopic road map mask image. Next, a fluoroscopy is implemented at a predetermined fixed position while the specimen is injected a contrast agent through his or her blood vessels. During the fluoroscopy, angiographic images obtained in the fluoroscopy are stored in a memory (not shown) provided in the image preparation section 9a of the image control unit 9, as needed. The image preparation section 9a adds plural fluoroscopic angiographic images stored in the memory. Since each of the angiographic images shows the injected contrast agent flowing in a different part of the blood vessels, the image preparation section 9a extracts only a peak part (which is enhanced by the contrast agent) of each stored image and traces only the peak part of each image. This may be called a peak trace. As a result, the image preparation section 9a prepares an image which represents all the blood vessels enhanced by the contrast agent. Such a prepared image is a reference mask image. After completion of the reference mask image, the contrast agent injection is terminated.

The image preparation section 9a implements a subtraction processing between the prepared reference mask image and fluoroscopic images being obtained in real time in the fluoroscopy. The fluoroscopic images are images which show only a background and the device. Therefore, as a result of the subtraction processing, images showing only contrast-enhanced blood vessels and the device are displayed in the display 10. In this display, in order to make it easier to distinguish between the blood vessels and the device, the image preparation section 9a may implement a display processing in which the blood vessels and the device are colored differently, such as, for example, in black and white. Accordingly, the doctor can easily forward the device, recognizing a position relationship between the inserted device and the blood vessels shown in the subtraction-processed image.

Since the fluoroscopic mask image is prepared as the road map based on the fluoroscopic angiographic images obtained at a fixed position by the fluoroscopy, the reference mask image has only one predetermined image field of view. Therefore, if it is a conventional X-ray diagnosis apparatus and its arm and/or its diagnostic table are moved during a real time fluoroscopy, the image field of view of the reference mask image does not become identical to all the image fields of view of the fluoroscopic images being obtained in real time since such fluoroscopic images are obtained from several image fields of view. This does not lead to a preferable subtraction processing. As a result, it is not easy to recognize the blood vessels and the device in the subtraction-processed images.

According to the X-ray diagnosis apparatus according to the fourth embodiment, even if the detector 3 is shifted during a real time fluoroscopy, information regarding the shifted distance and the shift direction is provided to the automatic panning control section 9c from the detector driving control section 1b. The automatic panning control section 9c converts the information into shift amounts of coordinates at a center of the reference mask image as information regarding shift amounts and shift directions of the reference mask image. The image preparation section 9a automatically shifts the reference mask image to positions based on the conversion results. Therefore, the image field of view of the reference mask image is corrected to become consistent with each image field of view of the fluoroscopic images being obtained in real time. Since the reference mask image appropriately shifted for each of the fluoroscopic images is used in the subtraction processing, preferable images can be displayed in the display 10.

As described above, according to the X-ray diagnosis apparatus in embodiments of the present invention, it can easily ensures a desired image field of view by shifting the detector 3, without moving the specimen lying on the table top 7a (i.e., without moving the table top 7a) and also without caring about interferences with peripheral equipments or the like. Further, since it is not necessary for the operator to manually move the very heavy arm 5, it is easy to adjust the arm position appropriately which requires a subtle adjustment. Therefore, the X-ray diagnosis apparatus according to embodiments of the present invention can reduce operator's loads for the position adjustment.

Still further, the X-ray diagnosis apparatus according to the embodiments of the present invention can automatically correct a deformation of images to be displayed in the display 10 depending on the shift of the detector 3. In addition, the X-ray diagnosis apparatus according to the embodiments of the present invention can automatically adjust center positions of the reference images to center positions of the images being obtained in real time. Similarly, the X-ray diagnosis apparatus according to the embodiments of the present invention can automatically adjust an image field of view of the road map mask image to image fields of view of the images being obtained in real time. Therefore, it makes it possible to provide the operator with images which are appropriate for proceeding with examinations.

The embodiments of the present invention described above are examples described only for making it easier to understand the present invention, and are not described for the limitation of the present invention. Consequently, each component and element disclosed in the embodiments of the present invention may be redesigned or modified to its equivalent within a scope of the present invention. Furthermore, any possible combination of such components and elements may be included in a scope of the present invention as long as an advantage similar to those obtained according to the above disclosure in the embodiments of the present invention is obtained.

What is claimed is:

1. An X-ray diagnosis apparatus for obtaining an X-ray image, comprising:
    an X-ray radiator configured to radiate an X-ray to a specimen;
    a detector configured to detect an X-ray data resulting from the X-ray;
    a first shifter mechanism coupled to the detector and configured to shift the detector along a detecting plane of the detector;
    a changer mechanism coupled to the X-ray radiator and configured to change a radiation direction of the X-ray against the detector;
    a controller configured to control the changer mechanism in accordance with the shift of the detector; and
    an image processor coupled to the detector and comprising a first fluoroscopic image data processing portion that prepares the X-ray image based on the detected X-ray data and a second fluoroscopic image data processing portion that corrects a deformation of the fluoroscopic image data.

2. The apparatus according to claim 1, wherein the changer mechanism rotates the X-ray radiator so as to change the radiation direction.

3. The apparatus according to claim 1, wherein the changer mechanism includes a collimator locatable relative to the X-ray radiator and configured to collimate the X-ray; and wherein the controller controls a position of the collimator.

4. The apparatus according to claim 3, wherein the controller further controls an aperture of the collimator.

5. The apparatus according to claim 1, further comprising a second shifter mechanism coupled to the X-ray radiator and configured to shift the X-ray radiator to a predetermined position.

6. The apparatus according to claim 1, further comprising an arm configured to support the detector through a detector supporter and to support the X-ray radiator; and wherein the first shifter mechanism shifts the detector relative to the detector supporter.

7. The apparatus according to claim 1, further comprising an arm configured to support the detector through a detector supporter and to support the X-ray radiator; and wherein the first shifter mechanism shifts the detector supporter coupled to the detector relative to the arm.

8. The apparatus according to claim 1, further comprising a designation device configured to designate the shift of the detector; an arm configured to support the detector through a detector supporter and to support the X-ray radiator; and wherein, when the designation device is operated to designate the detector to shift in a predetermined direction, the first shifter mechanism shifts the detector relative to the detector supporter in the predetermined direction and further shifts the detector supporter relative to the arm to help shift the detector in the predetermined direction.

9. The apparatus according to claim 1, further comprising a memory coupled to the image processor and configured to store a past image data; wherein the image processor is further configured to prepare, based on the past image data, a reference image data of a part of the specimen similar to what is viewed in the fluoroscopic image data in accordance with the shift of the detector.

10. The apparatus according to claim 9, wherein the reference image data is centered about a position corresponding to a center of the fluoroscopic image data in accordance with the shift of the detector.

11. The apparatus according to claim 9, further comprising a display configured to display the fluoroscopic image data and the reference image data.

12. The apparatus according to claim 1, further comprising a designation device configured to designate that the detector returns to an initial position.

13. The apparatus according to claim 1, wherein the first shifter mechanism shifts the detector in at least one of a first direction and a second direction perpendicular to the first direction.

14. The apparatus according to claim 1, further comprising a display coupled to the image processor and configured to display a processed image; wherein the image processor is further configured to prepare a contrast-enhanced reference image data prior to preparing the fluoroscopic image data; wherein the image processor is still further configured to perform a subtraction processing between the fluoroscopic image data and at least a part of the contrast-enhanced reference image data, the part being determined in accordance with the shift of the detector; and wherein the display provides a subtraction processed image as the processed image.

15. An X-ray diagnosis apparatus for obtaining an X-ray image, comprising:
an X-ray radiator configured to radiate an X-ray to a specimen;
a detector configured to detect an X-ray data resulting from the X-ray;
a shifter mechanism coupled to the detector and configured to shift the detector along a detecting plane of the detector;
an exposer mechanism coupled to the X-ray radiator and configured to cause the X-ray to be exposed throughout an effective detecting area of the detector;
a controller configured to control the second mechanism in accordance with the shift of the detector; and
an image processor coupled to the detector, the image processor having a memory configured to store a past image data and being configured to prepare a fluoroscopic image data based on the detected X-ray data and a reference image data, based on the past image data, of a part of the specimen similar to what is viewed in the fluoroscopic image data in accordance with the shift of the detector.

16. The apparatus according to claim 15, wherein the reference image data is centered about a position corresponding to a center of the fluoroscopic image data in accordance with the shift of the detector.

17. The apparatus according to claim 15, wherein the exposer mechanism rotates the X-ray radiator so as to cause the X-ray to be exposed throughout the effective detecting area.

18. The apparatus according to claim 15, wherein the exposer mechanism includes a collimator locatable relative to the X-ray radiator and configured to collimate the X-ray; and wherein the controller controls a position of the collimator.

19. The apparatus according to claim 18, wherein the controller further controls an aperture of the collimator.

20. The apparatus according to claim 15, wherein the exposer mechanism shifts the X-ray radiator to a predetermined position.

21. The apparatus according to claim 15, further comprising an arm configured to support the detector through a detector supporter and to support the X-ray radiator; and wherein the shifter mechanism shifts the detector relative to the detector supporter.

22. The apparatus according to claim 15, further comprising an arm configured to support the detector through a detector supporter and to support the X-ray radiator; and wherein the shifter mechanism shifts the detector supporter coupled to the detector relative to the primary supporter.

23. The apparatus according to claim 15, further comprising a designation device configured to designate the shift of the detector; an arm configured to support the detector through a detector supporter and to support the X-ray radiator; and wherein, when the designation device is operated to designate the detector to shift in a predetermined direction, the shifter mechanism shifts the detector relative to the detector supporter and further shifts the detector supporter relative to the arm to help shift the detector in the predetermined direction.

24. The apparatus according to claim 15, wherein the image processor is further configured to correct a deformation of the fluoroscopic image data in accordance with the shift of the detector.

25. The apparatus according to claim 15, further comprising a display configured to display the fluoroscopic image data and the reference image data.

26. The apparatus according to claim 15, further comprising a designation device configured to designate that the detector returns to an initial position.

27. The apparatus according to claim 15, wherein the shifter mechanism shifts the detector in at least one of a first direction and a second direction perpendicular to the first direction.

28. An X-ray diagnosis apparatus for obtaining an X-ray image, comprising:
an X-ray radiator configured to radiate an X-ray to a specimen;
a detector configured to detect an X-ray data resulting from the X-ray;
a set of gears coupled to the detector and configured to shift the detector along a detecting plane of the detector;

an X-ray radiator supporter coupled to the X-ray radiator and configured to move the X-ray radiator so as to cause the X-ray to be exposed throughout an effective detecting area of the detector;

a controller configured to control the X-ray radiator supporter in accordance with the shift of the detector;

an image processor coupled to the detector, the image processor having a memory configured to store one or more past fluoroscopic image data and being configured to prepare a current fluoroscopic image data based on the detected X-ray data and a contrast-enhanced reference image data based on at least one of the past fluoroscopic image data, and further to perform a subtraction processing between, the current fluoroscopic image data and at least a part of the contrast-enhanced reference image data, the part being determined in accordance with the shift of the detector; and a display coupled to the image processor and configured to display a subtraction processed image.

29. The apparatus according to claim 1, wherein the first shifter mechanism shifts the detector without concurrently shifting the X-ray radiator.

30. The apparatus according to claim 13, wherein the first shifter mechanism shifts the detector in both the first direction and the second direction perpendicular to the first direction.

31. The apparatus according to claim 15, wherein the shifter mechanism shifts the detector without concurrently shifting the X-ray radiator.

32. The apparatus according to claim 27, wherein the shifter mechanism shifts the detector in both the first direction and the second direction perpendicular to the first direction.

33. The apparatus according to claim 28, wherein the detector comprises a backside gear along a first direction of the detector.

34. The apparatus according to claim 33, wherein the detector further comprises another backside gear along a second direction of the detector perpendicular to the first direction.

* * * * *